(12) United States Patent
Sugita

(10) Patent No.: US 8,052,681 B2
(45) Date of Patent: Nov. 8, 2011

(54) HIGH-FREQUENCY INCISION INSTRUMENT FOR ENDOSCOPE

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 780 days.

(21) Appl. No.: 11/550,528

(22) Filed: Oct. 18, 2006

(65) Prior Publication Data

US 2007/0088354 A1  Apr. 19, 2007

(30) Foreign Application Priority Data

Oct. 19, 2005 (JP) ................................ 2005-303890

(51) Int. Cl.
*A61B 18/18* (2006.01)
(52) U.S. Cl. ............... 606/45; 606/46; 606/49; 606/167
(58) Field of Classification Search ................. 606/167, 606/172, 170, 106, 45–50, 1, 181; 604/164.01, 604/110, 117, 114; 215/320
See application file for complete search history.

(56) References Cited

U.S. PATENT DOCUMENTS

| | | | |
|---|---|---|---|
| 5,536,240 A * | 7/1996 | Edwards et al. | 604/22 |
| 5,843,091 A * | 12/1998 | Holsinger et al. | 606/108 |
| 6,193,717 B1 * | 2/2001 | Ouchi | 606/49 |
| 6,443,943 B1 * | 9/2002 | Ouchi | 606/1 |
| 6,613,002 B1 * | 9/2003 | Clark et al. | 600/593 |
| 2004/0172018 A1 * | 9/2004 | Okada | 606/46 |
| 2004/0254599 A1 * | 12/2004 | Lipoma et al. | 606/181 |
| 2005/0215853 A1 | 9/2005 | Ouchi | |
| 2006/0155271 A1 | 7/2006 | Sugita et al. | |
| 2006/0178656 A1 | 8/2006 | Sugita et al. | |
| 2006/0178657 A1 | 8/2006 | Sugita et al. | |
| 2006/0178669 A1 | 8/2006 | Sugita et al. | |

FOREIGN PATENT DOCUMENTS

| | | |
|---|---|---|
| JP | 3-015081 | 4/1991 |
| JP | 6-013741 | 4/1994 |
| JP | 2000-037455 | 2/2000 |
| JP | 2002-113016 | 4/2002 |
| JP | 2005-270240 | 10/2005 |
| JP | 2005-279126 | 10/2005 |

OTHER PUBLICATIONS

English Language Abstract of JP 2000-037455.
English Language Abstract of JP 2002-113016.
U.S. Appl. No. 11/550,508 to Sugita, filed Oct. 18, 2006.

* cited by examiner

*Primary Examiner* — Ryan Severson
*Assistant Examiner* — Tin Nguyen
(74) *Attorney, Agent, or Firm* — Greenblum & Bernstein, P.L.C.

(57) ABSTRACT

A high-frequency incision instrument for an endoscope configured to project forward and retreat, through a forward end portion of a flexible over tube, a rod electrode disposed close thereto by remote operation from an operating unit connected to a proximal end portion of the over tube. The high-frequency incision instrument includes a fixed stopper and a movable stopper located close to a forward end portion of the over tube and to a proximal end portion of the rod electrode respectively, to be butted to each other to define a maximum projection length of the rod electrode from the forward end portion of the over tube. The movable stopper is axially movable with respect to the rod electrode, and the operating unit includes a stopper position adjuster that adjusts by remote operation a distance between a farthest end portion of the rod electrode and the movable stopper.

6 Claims, 10 Drawing Sheets

HIGH-FREQUENCY INCISION INSTRUMENT FOR ENDOSCOPE

BACKGROUND OF THE INVENTION

The present invention relates to a high-frequency incision instrument for an endoscope.

A high-frequency incision instrument for an endoscope is inserted through an instrument insertion channel of the endoscope for incising a mucous membrane or another part of a human body when put to use, and is generally configured to project forward and retreat, through a forward end portion of a flexible over tube, a rod electrode disposed close thereto by remote operation from an operating unit connected to a proximal side of the over tube.

In such operation, the incision depth of the mucous membrane or another part varies depending on the state of the affected part to be incised, the environment of use of the high-frequency incision instrument and so forth. Accordingly, some high-frequency incision instruments are configured such that a maximum projection length of the rod electrode from the forward end portion of the over tube can be adjusted as desired, thereby enabling incising the affected part to a safe and optimal depth, for example as disclosed in Japanese Patent Provisional Publication No. 2002-113016 (hereinafter, referred to as '016 publication).

The high-frequency incision instrument according to '016 publication includes a pair of stoppers respectively disposed at a forward end portion of the over tube and a proximal end portion of the rod electrode so as to be butted to each other to thereby determine a maximum projection length of the rod electrode from the forward end portion of the over tube, and the control of the maximum projection length of the rod electrode is executed by adjusting a position of a forward mouthpiece screw-fitted on the forward end portion of the over tube.

However, the forward end portion of the over tube where the rod electrode is disposed is inserted into the body through the instrument insertion channel of the endoscope when the high-frequency incision instrument is in actual use. Accordingly, for adjusting the maximum projection length of the rod electrode in accordance with the state of the affected part, the high-frequency incision instrument has to be drawn out once through the instrument insertion channel, which often leads to troubles such as repeated adjustment procedures and losing track of the affected part.

To alleviate such troubles, it might be an option to provide a variable stopper that controls the maximum projection length of the rod electrode on the operating unit close to the operator, however when the high-frequency incision instrument is inserted through the endoscope which is serpentinely inserted in the body, the adjustment of the stopper performed on the proximal side is not correctly reflected in the resulting projection length of the rod electrode from the forward end portion of the over tube. Providing the stopper at a proximal position, therefore, is not effective in accurately adjusting the maximum projection length of the rod electrode.

SUMMARY OF THE INVENTION

Accordingly, aspects of the present invention provide a high-frequency incision instrument for an endoscope that allows adjusting as desired a maximum projection length of a rod electrode from a forward end portion of an over tube through operation at a proximal position, thereby facilitating incising a mucous membrane or another part always in a safe depth.

According to aspects of the invention, there is provided a high-frequency incision instrument for an endoscope configured to project forward and retreat, through a forward end portion of a flexible over tube, a rod electrode disposed close thereto by remote operation from an operating unit connected to a proximal end portion of the over tube, comprising a fixed stopper and a movable stopper located close to a forward end portion of the over tube and to a proximal end portion of the rod electrode respectively, to be butted to each other to define a maximum projection length of the rod electrode from the forward end portion of the over tube. The movable stopper is axially movable with respect to the rod electrode, and the operating unit includes a stopper position adjuster that adjusts by remote operation a distance between a farthest end portion of the rod electrode and the movable stopper, thereby enabling adjusting by manipulating the operating unit the projection length of the rod electrode from the forward end portion of the over tube defined when the movable stopper is butted to the fixed stopper.

In the above structure, the fixed stopper may be of a tubular shape and fixed to a farthest end portion of the over tube, so that the rod electrode can pass through the tubular body. Also, the over tube may include a conductive operating wire integrally connected to the rod electrode and disposed through inside the over tube over the entire length thereof, and such operating wire may be shielded in a flexible sheath integrally connected to the movable stopper, so that relatively moving the proximal end portion of the operating wire and the proximal end portion of the sheath in an axial direction by the stopper position adjuster changes the projection length of the rod electrode from the forward end portion of the over tube set when the movable stopper is butted to the fixed stopper.

The sheath may be a closely wound coil pipe made of a conductive material, and the movable stopper may be constituted of a forward facet of the coil pipe or a member attached to a forward end portion of the coil pipe. Alternatively, the sheath may be a flexible tube made of a non-conductive material, and the movable stopper may be constituted of a forward facet of the flexible tube or a member attached to a forward end portion of the flexible tube.

The operating unit may include a sliding member operable so as to cause the proximal end portion of the operating wire to axially slide with respect to the proximal end portion of the over tube. The proximal end portion of the sheath may be fixed to the sliding member, and the sliding member may be provided with a member to which the proximal end portion of the operating wire is connected, and thread-engaged therewith so as to rotate in a screwing motion around the axial line, and the member to which the proximal end portion of the operating wire is connected may serve as the stopper position adjuster.

Alternatively, operating unit may include a sliding member operable so as to cause the proximal end portion of the operating wire to axially slide with respect to the proximal end portion of the over tube, and the proximal end portion of the sheath may be fixed to the sliding member. The sliding member may be provided with a member to which the proximal end portion of the operating wire is connected, and attached thereto so as to be fixed at a desired position among a plurality of predetermined positions aligned in an axial direction, and the member to which the proximal end portion of the operating wire is connected may serve as the stopper position adjuster.

The sliding member may be provided with a connection terminal to which a high-frequency power cable is to be connected, and disposed so as to achieve electrical connection to the proximal end portion of the sheath, and the sheath may be fixed to the sliding member by the connection terminal.

The operating unit may include a sliding member operable so as to cause the proximal end portion of the operating wire to axially slide with respect to the proximal end portion of the over tube. The proximal end portion of the operating wire may be fixed to the sliding member, and the sliding member may be provided with a member to which the proximal end portion of the sheath is connected, and thread-engaged therewith so as to rotate in screwing motion around the axial line, and the member to which the proximal end portion of the sheath is connected may serve as the stopper position adjuster.

The sliding member may include a connection terminal to which a high-frequency power cable is to be connected, and disposed so as to achieve electrical connection to the proximal end portion of the operating wire, and the operating wire may be fixed to the sliding member by the connection terminal.

Further, graduations may be provided that indicates an adjustment status of a positional relationship between the relative positions of the proximal end portion of the operating wire and the proximal end portion of the sheath in an axial direction, being adjusted by the stopper position adjuster.

BRIEF DESCRIPTION OF THE ACCOMPANYING DRAWINGS

DETAILED DESCRIPTION OF THE EMBODIMENT

A high-frequency incision instrument for an endoscope, configured to project forward and retreat, through a forward end portion of a flexible over tube, a rod electrode disposed close thereto by remote operation from an operating unit connected to a proximal end portion of the over tube, is to include a fixed stopper and a movable stopper located close to a forward end portion of the over tube and to a proximal end portion of the rod electrode respectively, to be butted to each other to define a maximum projection length of the rod electrode from the forward end portion of the over tube. The movable stopper is set to axially move with respect to the rod electrode, and the operating unit is to include a stopper position adjuster that adjusts by remote operation a distance between a farthest end portion of the rod electrode and the movable stopper, thereby enabling adjusting by manipulating the operating unit the projection length of the rod electrode from the forward end portion of the over tube defined when the movable stopper is butted to the fixed stopper.

According to the embodiment, the high-frequency incision instrument for an endoscope includes the fixed stopper and the movable stopper located close to a forward end portion of the over tube and to a proximal end portion of the rod electrode respectively, to be butted to each other to define the maximum projection length of the rod electrode from the forward end portion of the over tube, thereby allowing adjusting a distance between a farthest end portion of the rod electrode and the movable stopper by operation from the operating unit. Such structure enables adjusting as desired the maximum projection length of the rod electrode from the forward end portion of the over tube by remote operation, thereby facilitating incising a mucous membrane or another part always in a safe depth.

Hereinafter, exemplary embodiments according to aspects of the invention will be described referring to the accompanying drawings.

Figure 3:
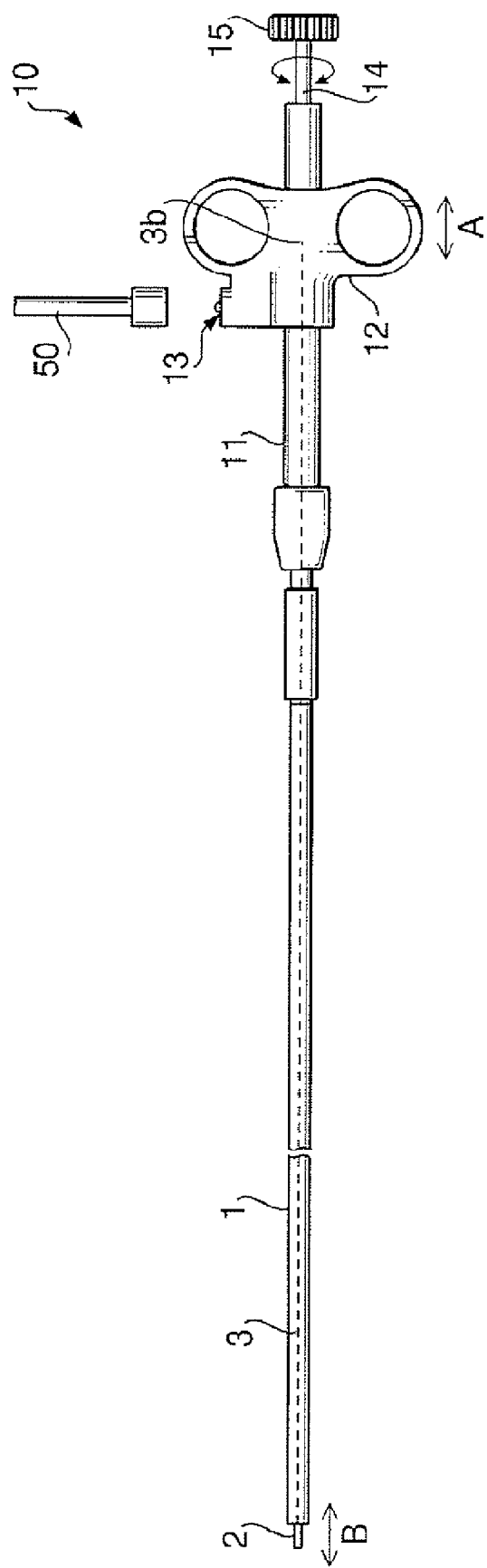
FIG. 3 is a side view showing an overall configuration of the high-frequency incision instrument for an endoscope according to the first embodiment.

FIG. 3 is a side view showing an overall configuration of the high-frequency incision instrument for an endoscope, in which an over tube 1 to be removably inserted in an instrument insertion channel of an endoscope (not shown) is flexible tube constituted of an electrically insulative material such as 4-ethylene fluoride resin. At a forward end portion of the over tube 1, a rod electrode 2 constituted of a conductive material such as a stainless steel wire is disposed so as to project out of and retreat into the over tube 1.

Inside the over tube 1, an operating wire 3 of a conductive material integrally connected to the rod electrode 2 is disposed throughout the entire length so as to move back and forth in an axial direction. Here, a tip portion of the operating wire 3 itself may be employed as the rod electrode 2, or the rod electrode 2 and the operating wire 3 may be separately prepared and integrally connected.

On the proximal side of the over tube 1, an operating unit 10 is provided, such that the proximal end portion of the over tube 1 is fixedly connected to a forward tip portion of an operating unit main body 11 of a slender shape in a back-and-forth direction (left-and-right direction in FIG. 3).

On the operating unit main body 11, a sliding manipulator 12 is mounted so as to slide back and forth, and a proximal end portion 3b of the operating wire 3 is connected to the sliding manipulator 12, so that moving the sliding manipulator 12 back and forth as indicated by the arrow A causes the rod electrode 2 to project from or retreat into the forward end portion of the over tube 1, as indicated by the arrow B. Numeral 13 designates a connection terminal to which a high-frequency power cable 50 is to be connected.

Although not shown in FIG. 3, at the forward end portion of the over tube 1a stopper is provided that delimits a maximum projection length of the rod electrode 2 from the forward end portion of the over tube 1. For the adjustment of the maximum projection length, a rotary adjusting rod 14 serving as the stopper position adjuster is disposed so as to project backward from a rear end portion of the operating unit 10, and an adjusting knob 15 is attached to the tip portion of the rotary adjusting rod 14.

Figure 1:
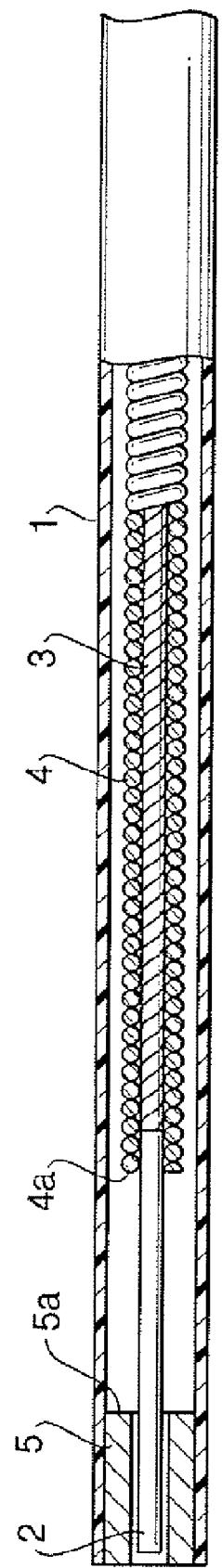
FIG. 1 is a side cross-sectional view of a forward end portion of a high-frequency incision instrument for an endoscope according to a first embodiment of the present invention, with the rod electrode retreated.

FIG. 1 depicts the forward end portion of the over tube 1, inside which a flexible sheath 4 constituted of a coil pipe of a closely wound stainless steel wire is inserted, so as to move back and forth together with the operating wire 3.

The flexible sheath 4 is fitted over the operating wire 3 over the entire length thereof, and relatively movable back and forth in an axial direction with respect thereto. It is to be noted however, that normally the operating wire 3 and the flexible sheath 4 axially move in an interlocked motion inside the over tube 1, because the flexible sheath 4 has an inner diameter that barely defines a gap with respect to the outer diameter of the operating wire 3, and the proximal end portion of the operating wire 3 and that of the flexible sheath 4 are usually held so as to inhibit a relative motion, on the side of the operating unit 10.

Inside the forward end portion of the over tube 1, a forward stopper 5 constituted of an electrically insulative material and formed in a tubular shape is firmly fixed, so that the rod electrode 2 passes through a hole provided along the axial line of the forward stopper 5. In the state shown in FIG. 1 in which the operating wire 3 is pulled toward the operating unit 10, the forward end portion of the rod electrode 2 is retreated into the forward stopper 5.

Figure 2:
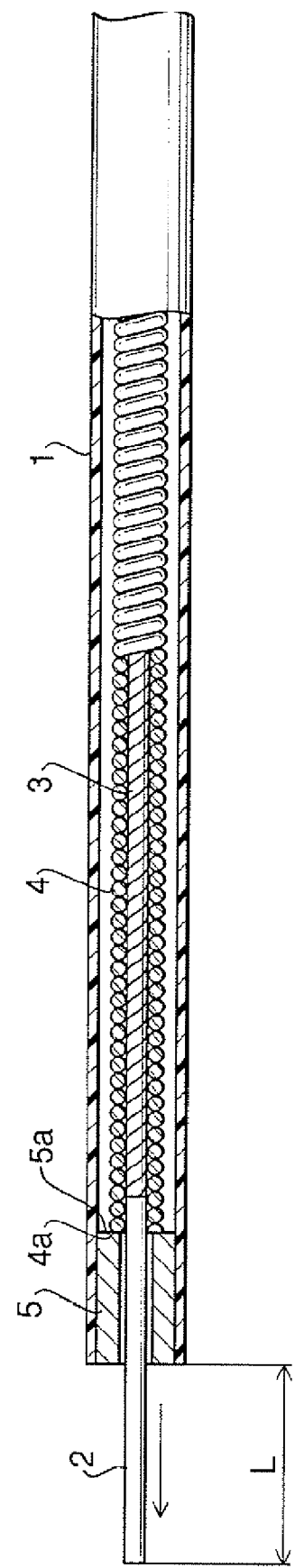
FIG. 2 is a side cross-sectional view of the forward end portion of the high-frequency incision instrument for an endoscope according to the first embodiment, with the rod electrode projected by a maximum length.

When the operating wire 3 is pushed forward from the side of the operating unit 10, a forward facet 4a of the flexible sheath 4 located close to the rod electrode 2 is butted to a rear facet 5a of the forward stopper 5 as shown in FIG. 2, so that the rod electrode 2 is inhibited from projecting farther from the forward end portion of the over tube 1, and the projection length L under such state (i.e. the maximum projection length) delimits the incision depth of the mucous membrane.

Accordingly, the rear facet 5a of the forward stopper 5 and the forward facet 4a of the flexible sheath 4 act as the fixed stopper and the movable stopper respectively, so as to delimit the maximum projection length L of the rod electrode 2. Here, a member may be fixed to the forward end portion of the flexible sheath 4, so that the member serves as the movable stopper.

Figure 4:
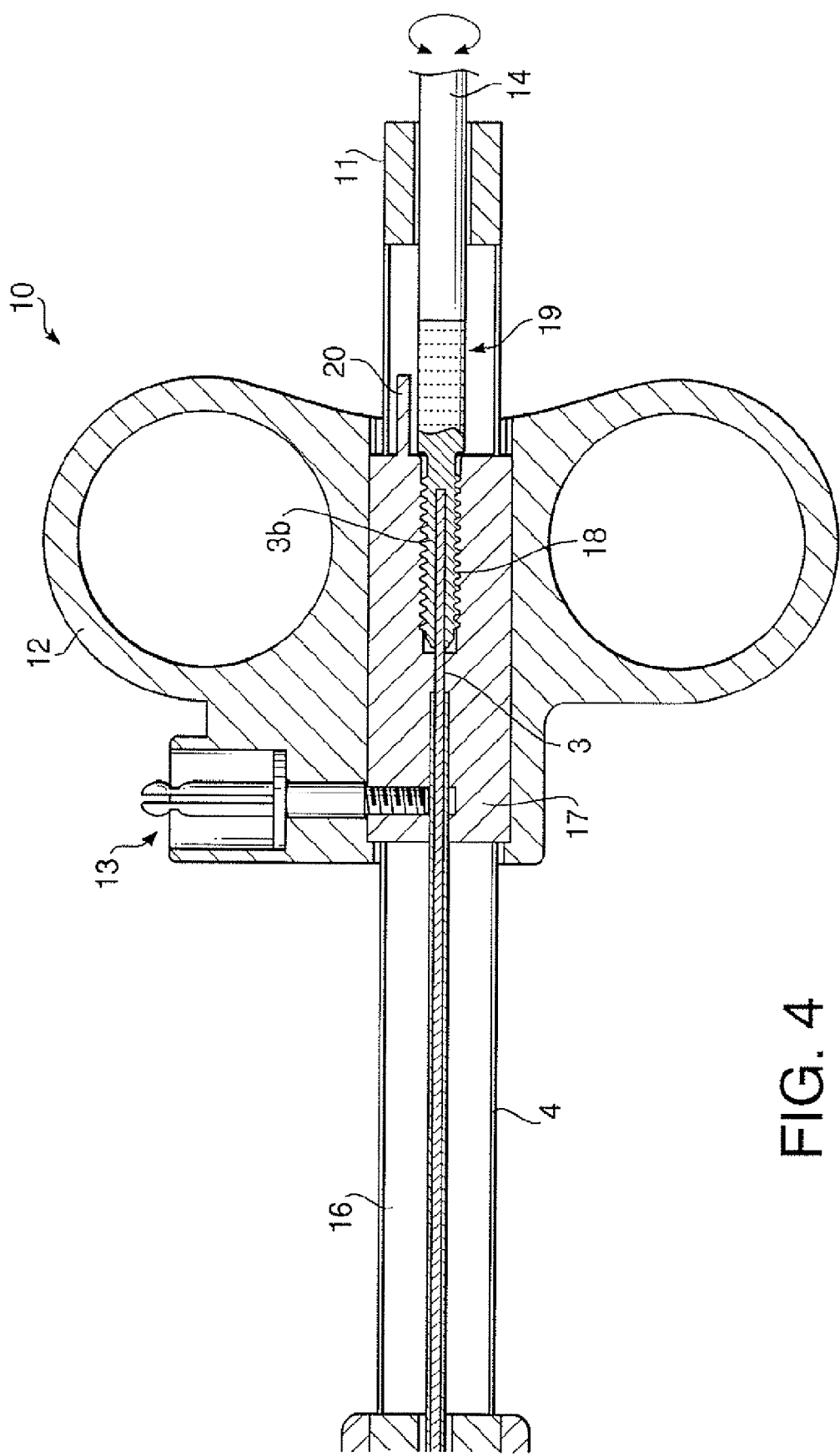
FIG. 4 is a fragmentary side cross-sectional view of an operating unit of the high-frequency incision instrument for an endoscope according to the first embodiment.

FIG. 4 is an enlarged view of a part of the operating unit 10. The operating unit main body 11 includes a slit 16 axially formed over a sufficient length, in which a sliding member 17 is slidably fitted, and the sliding member 17 and the sliding manipulator 12 are integrally coupled by the connection terminal 13. Here, another member than the connection terminal 13 may be employed for coupling the sliding member 17 and the sliding manipulator 12.

The connection terminal 13 is screwed into the sliding member 17 thus to be fixed thereto, such, that the tip portion of the screw presses the flexible sheath 4 against the sliding member 17 thus to detain the flexible sheath 4. Accordingly, the connection terminal 13 and the coil pipe flexible sheath 4 are electrically continuous, and hence a current runs from the high-frequency power cable 50 to the rod electrode 2, via the connection terminal 13 and the flexible sheath 4.

The rotary adjusting rod 14, which serves as the stopper position adjuster, is disposed such that the axial line coincides with an extension of the proximal end portion of the operating wire 3, which is fixedly connected to the forward end portion of the rotary adjusting rod 14 by brazing or the like, and a portion close to the forward tip portion of the rotary adjusting rod 14 is thread-engaged with a screw hole formed on the sliding member 17. Numeral 18 designates the screw-engaging portion.

Here, the proximal end portion 3b of the operation wire 3 may be connected to the rotary adjusting rod 14 by any desired means, however it is preferable to permit relative rotation between the rotary adjusting rod 14 and the operating wire 3 around the axial line, because the rotation of the rotary adjusting rod 14 can be kept from being transmitted to the operating wire 3.

Figure 5:
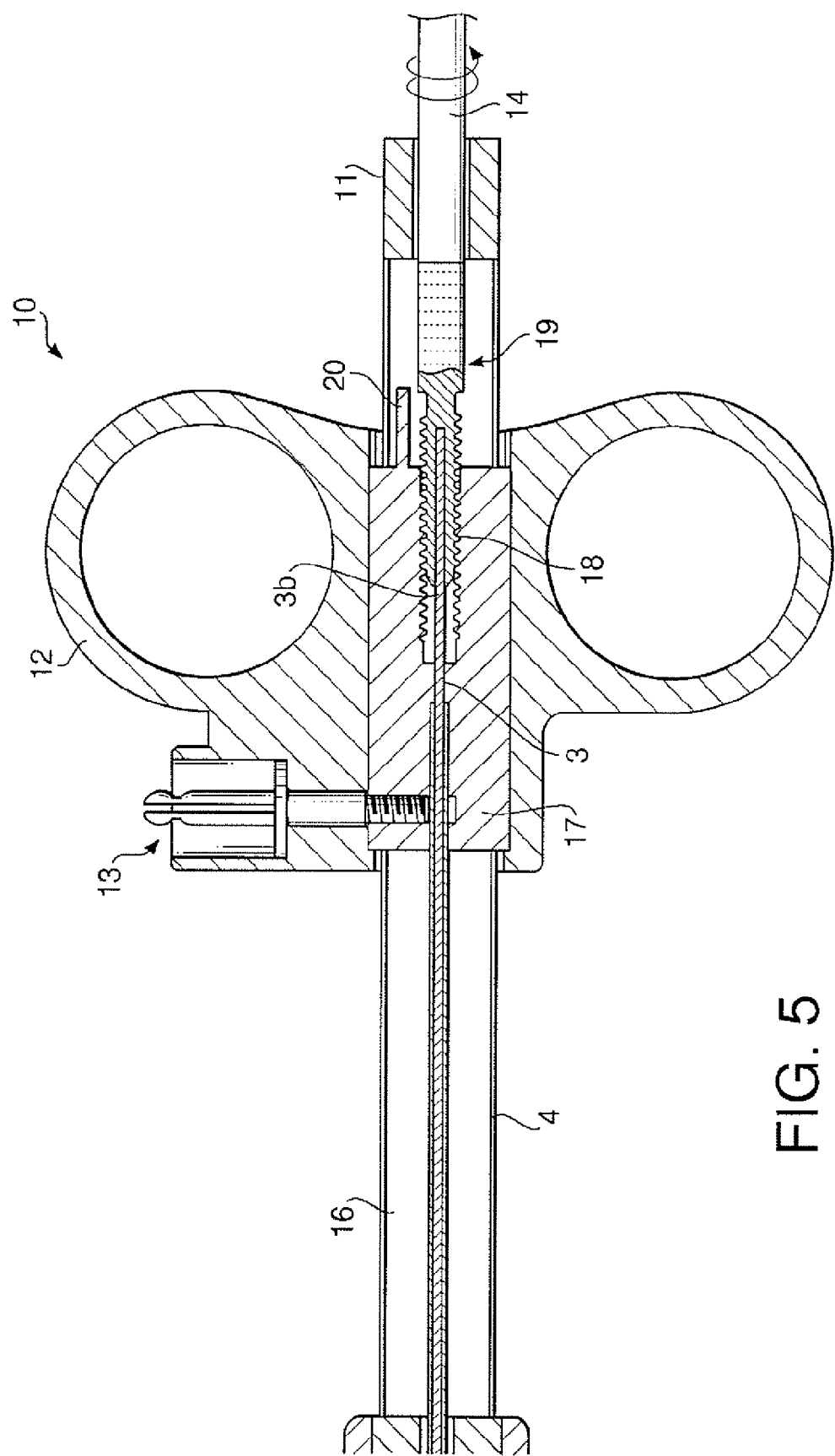
FIG. 5 is a fragmentary side cross-sectional view of a high-frequency incision instrument for an endoscope according to the first embodiment, with the rod electrode adjusted for a reduced maximum projection length.

When the adjusting knob 15 shown in FIG. 3 is manipulated so as to rotate the rotary adjusting rod 14 configured as above around the axial line, the rotary adjusting rod 14 rotates with respect to the sliding member 17 thereby moving in an axial direction, and hence the proximal end portion 3b of the operating wire 3 axially moves with respect to the proximal end portion of the flexible sheath 4, as shown in FIG. 5.

Figure 6:
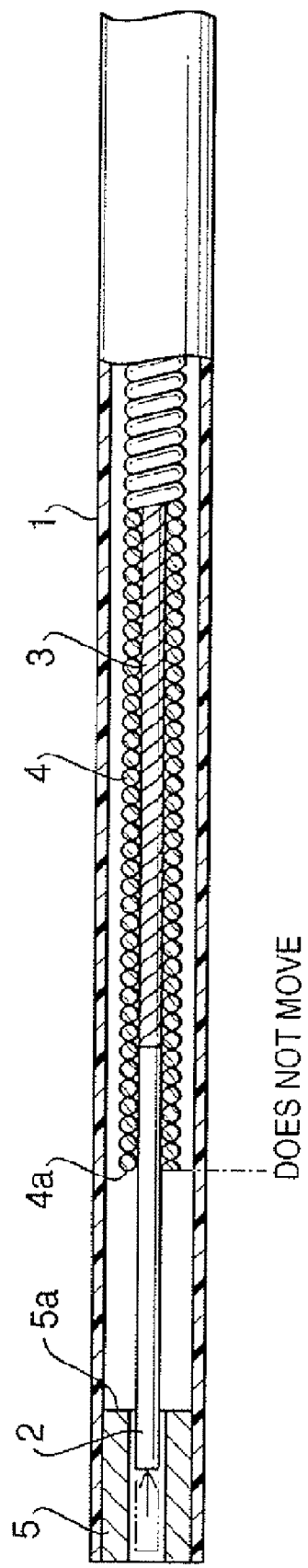
FIG. 6 is a fragmentary side cross-sectional view of the forward end portion of the high-frequency incision instrument for an endoscope according to the first embodiment, with the rod electrode adjusted for a reduced maximum projection length and retreated.
Figure 7:
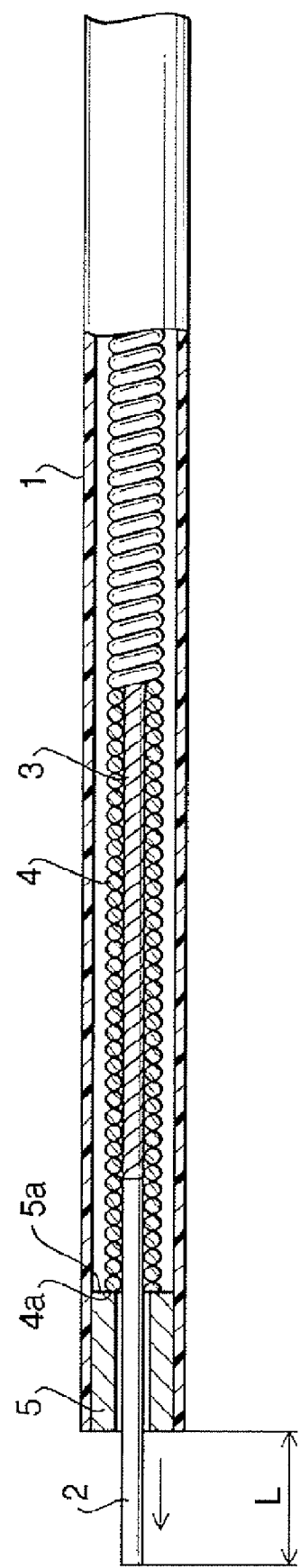
FIG. 7 is a fragmentary side cross-sectional view of the forward end portion of the high-frequency incision instrument for an endoscope according to the first embodiment, with the rod electrode adjusted for a reduced maximum projection length and projected by a maximum length.

Such motion originates a change of the distance between the forward facet 4a of the flexible sheath 4 and the farthest end portion of the rod electrode 2 inside the forward end portion of the over tube 1, as shown in FIG. 6. Accordingly, as shown in FIG. 7, the projection length L of the rod electrode 2 from the forward tip portion of the over tube 1, defined when the forward facet 4a of the flexible sheath 4 serving as the movable stopper is butted to the forward stopper 5 (i.e. the maximum projection length), is also changed.

Therefore, the maximum projection length L of the rod electrode 2 from the forward end portion of the over tube 1 can be adjusted as desired by remote operation from the side of the operating unit 10, without the need to drawing out each time the high-frequency incision instrument from the instrument insertion channel of the endoscope.

Referring back to FIGS. 4 and 5, graduations 19 are provided on an outer circumferential surface of the rotary adjusting rod 14, so as to indicate a relative travel distance in an axial direction between the rotary adjusting rod 14 and the sliding member 17 (i.e. positional relationship in an axial direction between the proximal end portion 3b of the operating wire 3 and the proximal end portion of the flexible sheath 4). Numeral 20 designates is an index piece provided on the sliding member 17, for indicating a position on the graduations 19.

The high-frequency incision instrument for an endoscope thus configured enables, even when the endoscope through which the over tube 1 is inserted is serpentinely inserted into a human body, adjusting the maximum projection length L of the rod electrode 2 accurately to a desired length whenever necessary, by operation at hand while confirming the actual status through the endoscope.

Figure 8:
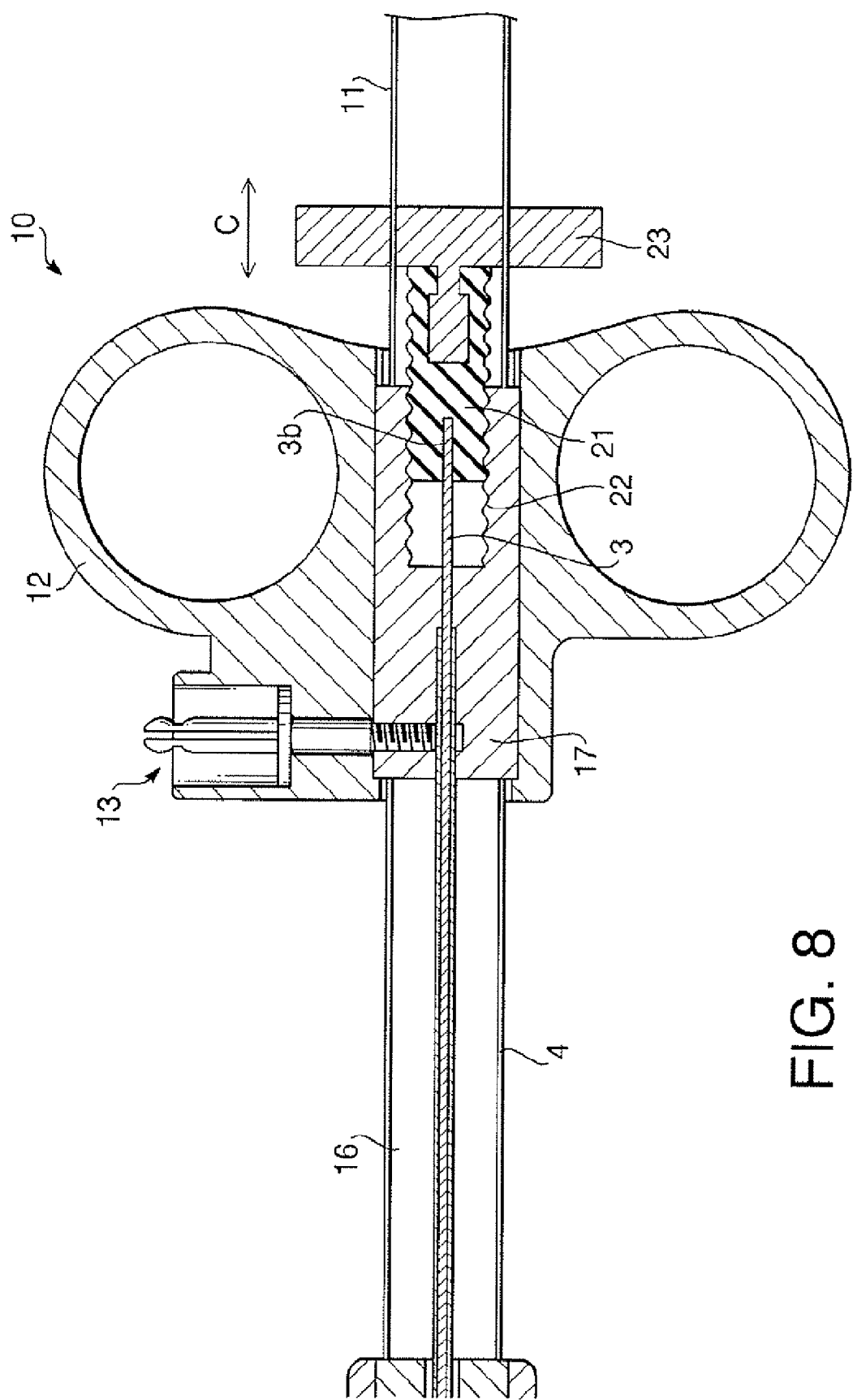
FIG. 8 is a fragmentary side cross-sectional view of an operating unit of a high-frequency incision instrument for an endoscope according to a second embodiment of the present invention.

FIG. 8 depicts the operating unit of a high-frequency incision instrument for an endoscope according to a second embodiment of the present invention, in which a fitting rod 21 constituted of an elastic material is attached to the proximal end portion of the operating wire 3, so as to serve as a stopper position adjuster that can be relatively moved in an axial direction with respect to the sliding member 17.

The outer circumferential surface of the fitting rod 21 is of a rippled shape with alternately repeating major diameter portions and minor diameter portions, to be fitted in a fitting hole 22 formed on the sliding member 17 in a similar profile, and an adjusting knob 23 is attached to the rear end portion of the fitting rod 21 so as to protrude from the operating unit main body 11. In this case also, it is preferable to provide graduations on the outer surface of the fitting rod 21, as in the first embodiment.

With such configuration of the operating unit 10 of the high-frequency incision instrument for an endoscope according to this embodiment, axially moving the adjusting knob 23 with an appropriate force with respect to the sliding manipulator 12 as indicated by the arrow C causes the fitting rod 21 to be elastically deformed and thus to axially move inside the fitting hole 22, and then to be fixed at a desired position among a plurality of positions where the rippled profile of the fitting rod 21 and that of the fitting hole 22 match with each other, thus allowing adjusting the maximum projection length L of the rod electrode 2.

Figure 9:
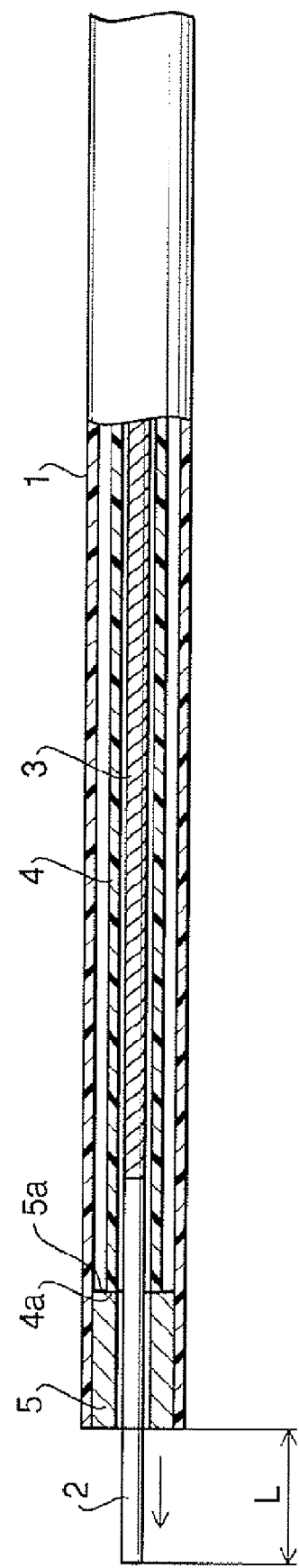
FIG. 9 is a side cross-sectional view of a forward end portion of a high-frequency incision instrument for an endoscope according to a third embodiment of the present invention, with the rod electrode projected by a maximum length.

FIG. 9 depicts a forward end portion of a high-frequency incision instrument for an endoscope according to a third embodiment of the present invention, in which the flexible sheath 4 is constituted of a flexible tube such as a 4-ethylene fluoride resin tube, and a forward facet 4a thereof serves as the movable stopper. On the forward part, that is the only difference from the first embodiment. Alternatively, a separate member that can serve as the movable stopper may be attached to the forward end portion of the flexible sheath 4.

Figure 10:
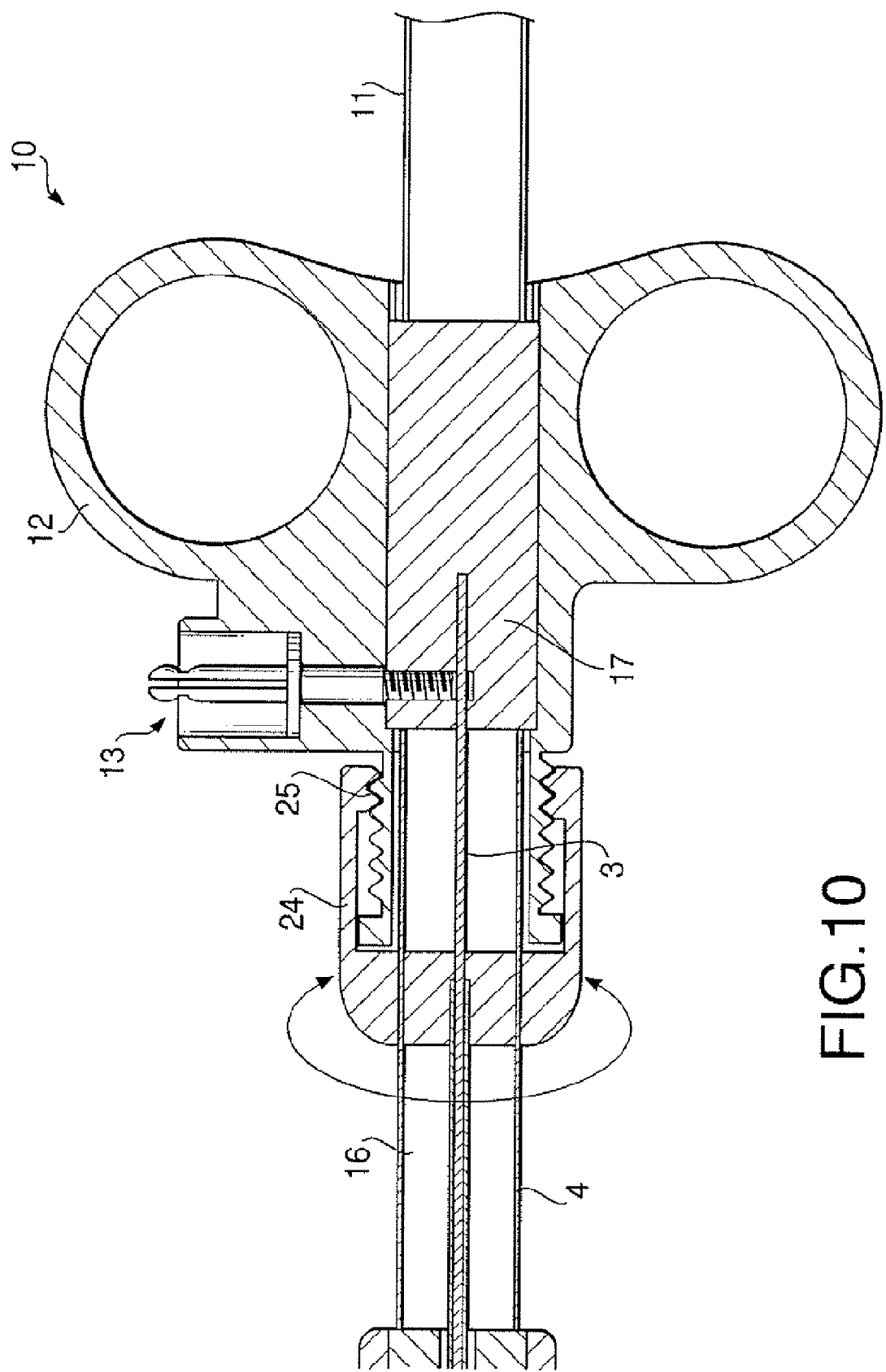
FIG. 10 is a fragmentary side cross-sectional view of an operating unit of a high-frequency incision instrument for an endoscope according to the third embodiment.

FIG. 10 depicts the operating unit 10 of the high-frequency incision instrument for an endoscope configured as above, according to the third embodiment. Since the flexible sheath 4 is not conductive, the proximal end portion of the operating wire 3, which is conductive, is pressed by the tip portion of the connection terminal 13 against the sliding member 17 to be fixed thereto, thus achieving electrical connection between the operating wire 3 and the connection terminal 13.

Also, an adjusting nut 24 of a cap nut type, to which the proximal end portion of the flexible sheath 4 is connected, is provided so as to rotate in a screwing motion around the axial line, and thread-engaged with a male-threaded portion formed on the sliding manipulator 12 which integrally moves with the sliding member 17. Numeral 25 designates such screw-engaging portion. Accordingly, rotating the adjusting nut 24 around the axial line can axially move the proximal end portion of the flexible sheath 4 with respect to the proximal end portion of the operating wire 3, thereby enabling adjusting the maximum projection length L of the rod electrode 2.

Further, the operating unit 10 shown in FIG. 10 may also be employed as the operating unit of the first embodiment in which the flexible sheath 4 is constituted of the coil pipe. In addition, graduations similar to those of the first embodiment may be provided close to the screw-engaging portion 25.

The present disclosure relates to the subject matter contained in Japanese Patent Application No. 2005-303890, filed on Oct. 19, 2005, which is expressly incorporated herein by reference in its entirety.

What is claimed is:

1. A high-frequency incision instrument for an endoscope, comprising:
a flexible over tube;
an operating unit connected to a proximal end portion of the over tube;
a rod electrode that projects out of and retreats into a forward end portion of the flexible over tube, based on a remote operation of the operating unit;
a fixed stopper located close to the forward end portion of the over tube;
a conductive operating wire integrally connected to the rod electrode and disposed inside the over tube over the entire length thereof; and
a flexible sheath fitted over the operating wire, a forward facet of the flexible sheath located close to a proximal end portion of the rod electrode functioning as a movable stopper,
wherein the fixed stopper and the movable stopper butt against each other to define a maximum projection length of the rod electrode from the forward end portion of the over tube,
the movable stopper is axially movable with respect to the rod electrode,
the operating unit includes a stopper position adjuster that adjusts, by remote operation, a distance between a farthest end portion of the rod electrode and the movable stopper by moving the movable stopper with respect to the rod electrode, thereby enabling an adjustment of the maximum projection length of the rod electrode from the forward end portion of the over tube, by manipulating the operating unit,
relatively moving a proximal end portion of the operating wire and a proximal end portion of the sheath in an axial direction by the stopper position adjuster changes the maximum projection length of the rod electrode from the forward end portion of the over tube defined when the movable stopper is butted to the fixed stopper,
the operating unit includes a sliding member operable so as to cause the proximal end portion of the operating wire to axially slide with respect to a proximal end portion of the over tube,
the proximal end portion of the operating wire is fixed to the sliding member, and
the stopper position adjuster comprises a cap nut-type adjusting nut which is connected to the proximal end portion of the sheath, and which thread-engages with a portion of the sliding member so as to rotate in a screwing motion around an axis of the sliding member.

2. The high-frequency incision instrument for an endoscope according to claim 1, wherein the fixed stopper has a tubular body and is fixed to a farthest end portion of the over tube, so that the rod electrode passes through the tubular body.

3. The high-frequency incision instrument for an endoscope according to claim 1, wherein the sliding member is provided with a connection terminal to which a high-frequency power cable is to be connected, disposed so as to achieve electrical connection to the proximal end portion of the operating wire.

4. The high-frequency incision instrument for an endoscope according to claim 3, wherein the operating wire is fixed to the sliding member by the connection terminal.

5. The high-frequency incision instrument for an endoscope according to claim 1, further comprising graduations that indicate an adjustment status of a positional relationship between the proximal end portion of the operating wire and the proximal end portion of the sheath in an axial direction, being adjusted by the stopper position adjuster.

6. The high-frequency incision instrument for an endoscope according to claim 1, wherein a slight gap is provided between an inner diameter of the flexible sheath and an outer diameter of the operating wire.

* * * * *